United States Patent [19]

Fischer

[11] 4,116,675
[45] Sep. 26, 1978

[54] PYRIDINIUM-S-TRIAZINES FOR REGULATING PLANT GROWTH

[75] Inventor: Hanspeter Fischer, Bottmingen, Switzerland

[73] Assignee: Ciba-Geigy Corporation, Ardsley, N.Y.

[21] Appl. No.: 791,267

[22] Filed: Apr. 27, 1977

[30] Foreign Application Priority Data

May 4, 1976 [CH] Switzerland .................. 5553/76

[51] Int. Cl.² ............... A01N 9/22; C07D 251/16
[52] U.S. Cl. ........................... 71/93; 544/180; 71/74; 71/76
[58] Field of Search ............... 71/93, 74, 76; 260/248 R, 248 CS

[56] References Cited

U.S. PATENT DOCUMENTS

| | | | |
|---|---|---|---|
| 3,510,483 | 5/1970 | Trepanier | 71/93 X |
| 3,544,570 | 12/1970 | Timmler et al. | 71/93 X |
| 3,682,617 | 8/1972 | Doyle, Jr. | 71/94 |
| 3,737,299 | 6/1973 | Hedrich | 71/94 |
| 3,804,612 | 4/1973 | Hedrich | 71/94 |
| 3,901,678 | 8/1975 | Fischer | 71/74 |

*Primary Examiner*—Catherine L Mills
*Attorney, Agent, or Firm*—Harry Falber

[57] ABSTRACT

2-Pyridinium-s-triazine salts of the formula

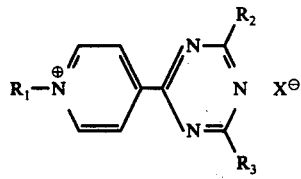

wherein $R_1$ represents unsubstituted or substituted alkyl of from 1 to 12 carbon atoms, alkenyl or haloalkenyl, $R_2$ and $R_3$ independently represent hydrogen, lower alkyl or haloalkyl and $X^\ominus$ is the anion of an inorganic or organic acid. These salts are growth regulating agents especially for defoliation and desiccation of crop plants in order to facilitate harvesting. They may also be used as post-emergent herbicides.

13 Claims, No Drawings

PYRIDINIUM-S-TRIAZINES FOR REGULATING PLANT GROWTH

The present invention provides quaternary salts which regulate plant growth and in particular have desiccating, defoliating and herbicidal action, a process for their manufacture, also compositions and a method of regulating plant growth, chiefly a method of desiccating and defoliating parts of plants above the ground as well as of controlling weeds, which comprises the use of said quaternary salts as active compounds.

The novel quaternary salts have the formula

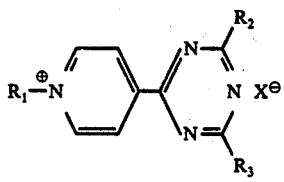

(I)

wherein $R_1$ represents a straight-chain or branched alkyl group of 1 to 12 carbon atoms which can be substituted by halogen, alkoxy, cyano, phenyl, carboxyl, alkoxycarbonyl, alkylcarbonyl, aminocarbonyl, mono- and dialkylaminocarbonyl, and also represents an alkenyl or halogenalkenyl group, each of $R_2$ and $R_3$ independently represents a hydrogen atom or a lower alkyl or halogenalkyl group of 1 to 4 carbon atoms, and X represents the anion of an inorganic or organic acid.

By alkyl groups $R_1$ are meant, for example, the following straight-chain and branched groups: methyl, ethyl, n-propyl, isopropyl, n-butyl, isobutyl, sec.-butyl, tert.-butyl, n-pentyl, n-hexyl, n-octyl, n-dodecyl and the isomers of the $C_5$–$C_{12}$-alkyl groups. The lower straight-chain or branched alkyl groups in particular, i.e. those having 1 to 4 carbon atoms, form the alkyl moiety of alkoxy, alkylcarbonyl and alkoxycarbonyl groups which form substituents. Halogenated alkyl groups are preferably groups having 1 to 4 carbon atoms which can be mono- or polysubstituted by halogen, in particular fluorine. The $CF_3$ group is particularly preferred. Alkenyl groups can be straight-chain or branched and have from 3 to 7 carbon atoms. Such groups can be propenyl, butenyl, pentenyl, hexenyl and heptenyl groups. The allyl and methallyl groups are preferred. If an alkyl group $R_1$ carries functional substituents, such as alkoxy, cyano, carboxyl, alkoxycarbonyl, alkylcarbonyl, aminocarbonyl, and also phenyl groups, it is primarily a lower alkyl group which has preferably only 1 carbon atom. The symbol X which represents the anion of an inorganic or organic acid can be, for example, the anion of the following acids: hydrohalic acids, such as hydrochloric or hydrobromic acid, hydroiodic acid, phosphoric acid, thio- and dithiophosphoric acid, sulphuric acid, fluoroboric acid (HBF$_4$), perchloric acid, alkylsulphuric acids, such as methyl- or ethylsulphuric acid, arylsulphuric acids, such as benzenesulphonic acid or p-toluenesulphonic acid, naphthoic acid, benzoic acid, halobenzoic acids, acetic acid, haloacetic acids, aminoacetic acid, propionic acid, halopropionic acids, butyric acid, lactic acid, stearic acid, aliphatic dicarboxylic acids, such as oxalic acid, tartaric acid, maleic acid, and also fluorosulphuric acid or carboxylic acids which have a defoliating or desiccating action, for example 3,6-epoxycyclohexane-1,2-dicarboxylic acid, 3-haloacrylic acids or 2,3,5,5,5-pentachloro-4-oxo-pentenoic acid. In addition, X can represent the anion $I_3^{\ominus}$ or $Br_3^{\ominus}$.

Preferred compounds of the formula I are those wherein $R_1$ represents a lower alkyl group which is unsubstituted or substituted by alkoxycarbonyl, each of $R_2$ and $R_3$ represents hydrogen and $X^{\ominus}$ is a halogen anion or the anion $Br_3^{\ominus}$ or $CH_3OSO_2O^{\ominus}$.

Related 4-substituted monopyridilium salts are already known from U.S. Pat. Nos. 3,737,299, 3,804,612 and 3,682,617.

The novel quaternary salts of the formula I are obtained by quaternisation, in a manner known per se, of the 2-pyridyl-s-triazines from which they are derived of the formula II

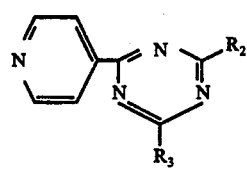

(II)

wherein $R_2$ and $R_3$ are as defined in formula I. One molar equivalent of a compound of the formula $$R_1 - X$$

wherein $R_1$ is as defined in formula I and $X$ represents a halogen atom, an alkylsulphonyloxy, alkoxysulphonyloxy, arylsulphonyloxy or fluorosulphonyloxy group, is used as quaternising agent for alkylating or alkenylating the pyridyl radical.

It is advantageous to carry out the quaternisation in the presence of a solvent or diluent which is inert to the reactants, such as an aromatic hydrocarbon, for example benzene, toluene or xylenes, a chlorinated hydrocarbon, for example chlorobenzene, methylene chloride, chloroform, a N-alkylated acid amide, such as dimethyl formamide; sulphoxides, such as dimethyl sulphoxide; nitriles, such as acetonitrile; ketones, such as acetone or methyl ethyl ketone; alcohols, especially lower alkanols, ethers, and ethereal compounds, water, or mixtures of such solvents with one another. The quaternising temperatures are between −50° C. and +200° C. The reaction times are from 15 minutes to several days and depend largely on the reactivity of the reactants and the solvent employed. The reaction can also be carried out in an autoclave under pressure. The resultant quaternary salts can be reacted with other non-phytotoxic inorganic or organic acids in order to exchange the anion of a possibly phytotoxic acid.

For example, the halogen ion of a resultant quaternary pyridylium halide can be easily exchanged for the anion of any other inorganic or organic acid, namely (a) by converting the halide into the hydroxide with subsequent neutralisation with the corresponding acid, (b) by treating the halide or hydroxide with an anion exchanger, or, if an iodine ion is present, (c) by reaction with $I_2$ or $Br_2$ to form $I_3^{\ominus}$ and $Br_3^{\ominus}$.

A number of the starting materials of the formula II are known, such as 2-(4'-pyridyl)-4,6-bis-trichloromethyl-s-triazine (German Pat. No. 1,200,314) and 2-(4'-pyridyl)-4,6-bis-methyl-s-triazine (Bull. Chem. Soc. Jap. 1973, Vol. 46, p. 2809).

Most of the mono-pyridyl-s-triazine starting materials of the formula II are thus also novel compounds which, however, can be easily prepared from 4-cyanopyridine by methods which are known per se. To obtain starting materials of the formula II, in which each of $R_2$ and $R_3$ is a hydrogen atom, the cyclisation to give the s-triazine ring must be carried out in alkaline medium, so that bis-pyridyl-triazines are not formed.

(1) Preparation of starting materials of the formula II, in which $R_2 = R_3$. One mole of 4-carbalkoxypyridine or 4-amidino-pyridine (III) or a salt thereof or one mole of a 4-alkoxy-carboximidoyl-pyridine (IV) of the formula

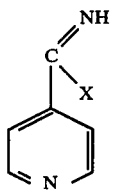  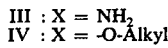

III : X = $NH_2$
IV : X = -O-Alkyl prepared from 4-cyanopyridine by direct reaction with ammonia (→ III) or with an alkanol (→ IV), or by reaction of IV with ammonia (→ III) is cyclised (a) with a triazine of the formula

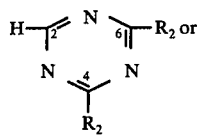

(b) with an ammonium salt of 2-azapropenylidene (Angew. Chemie 72, 956) of the formula

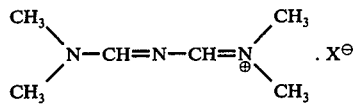

(X = an anion, such as a halide) or
(c) with an amidino compound

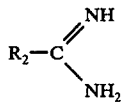

or with an excess of a salt, or finally
(d) with an alkoxycarbonimidoyl compound

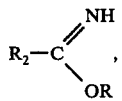

to give the 2-(4'-pyridyl)-s-triazine of the formula II, wherein the 4- and 6-positions carry the same substituent $R_2$. Preferably, this cyclisation reaction is carried out under alkaline conditions.

(2) Preparation of starting materials of the formula II, wherein $R_2$ and $R_3$ are not identical. 4-Amidino-pyridine (III) or 4-alkoxy-carbimidoyl-pyridine (IV) is converted by acylation into an often non-insoluble intermediate compound of the formula Va or Vb respectively

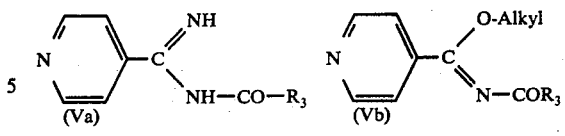

For this reaction it is possible to use acids and anhydrides, acid chlorides, acid amides, esters, ester amides, orthoesters, aminoacetals of the formulae $R_3COOH$, $R_3COCl$, $R_3COOR$, $R_3CONH_2$, $R_3$—$C(OR)_3$,

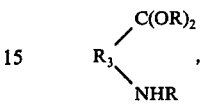

and also iminoethers, nitriles, amidines or chloroiminium salts of the type $(CH_3)_2N^\oplus = CH.X$, in each of which R represents an alkyl group.

The intermediates (Va) and (Vb) are finally cyclised with an amidino compound

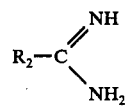

to give the desired 2-(4'-pyridyl)-s-triazine of the formula II with different substituents $R_2$ and $R_3$. Unsymmetrically substituted triazines can also be prepared by co-trimerisation of (III) with amidines

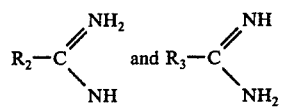

or with corresponding iminoethers

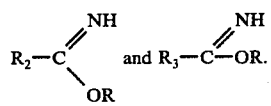

The preferred reaction for preparing unsymmetrically substituted starting materials of the formula II proceeds in accordance with the following equation:

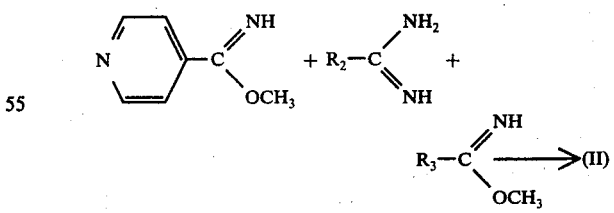

All the above reactions can be carried out in the presence or absence of a catalyst. Suitable catalysts are chiefly bases, such as tertiary amines, alkali hydroxide, alkali alcoholates, sodium hydride, and others. The choice of catalyst depends in the individual case on the reactants. Iminoethers and amidines may also be used for these reactions in form of their salts, such as hydrochlorides.

The starting materials are known or they can be prepared by methods which are known per se.

For example, 4-aminopyridine and its salts are known from J. Am. Chem. Soc. 75, 1933–1942 (1953) and J. Org. Chem. 19, 753–757 (1954). This compound is obtained by converting 4-cyanopyridine with an alkanol, such as ethanol, into the corresponding iminoether (imidate) and heating this latter with aqueous ammonium chloride solution.

The following Examples illustrate a number of processes for manufacturing the pyridinium-s-triazine salts of the present invention of the formula I.

EXAMPLE 1

(a) 2-(4'-Pyridyl)-s-triazine 1.0 g of sodium and then 104 g of 4-cyanopyridine (1 mole) are dissolved at room temperature in 500 ml of absolute methanol and the solution is subsequently stirred for 6 hours at 25°–30° C. Then 162 g of sodium methylate (3 moles) and a solution of 240 g of formamidine hydrochloride (3 moles) in 500 ml of absolute dimethyl formamide are added at 25°–30° C. After the reaction mixture has been stirred for 16 hours at 25°–30° C., it is refluxed for 6 hours at 100° C. bath temperature. After it has cooled, the mixture is concentrated by rotary evaporation and the residue is diluted with 4 liters of water. The precipitate is collected with suction and the filter residue is washed with water and dried in vacuo at 80° C., giving 121.4 g of 2-(4'-pyridyl)-s-triazine (77% of theory) with a melting point of 189°–191° C.

| Analysis: | $C_8H_6N_4$ (M = 158.16) | | |
|---|---|---|---|
| | C | H | N |
| calculated: | 60.75 | 3.83 | 35.42% |
| found: | 60.57 | 3.55 | 35.50% |

(b) 2-(N'-ethyl-4'-pyridilium)-s-triazine-bromide

To a mixture of 96.4 g (0.61 mole) of 2-(4'-pyridyl)-s-triazine and 1 liter of absolute ethanol are added 100 ml of absolute dimethyl formamide and 130 ml of ethyl bromide. After boiling for 20 hours at 100° C. bath temperature, the mixture is concentrated. The residual oily substance is boiled 4 times with 150 ml of acetone and filtered off. The filter residue is dried, to give 107.4 g (66% of theory) of 2-(N'-ethyl-4'-pyridylium)-s-triazine-bromide with a melting point of 188°–191° C.

EXAMPLE 2

2-(N'-Methyl-4'-pyridylium)-s-triazine-bromide

In a pressure autoclave, 28.4 g (0.18 mole) of 2-(4'-pyridyl)-s-triazine (0.18 mole), 22.8 g (0.2 mole) of methyl bromide and 150 ml of absolute dimethyl formamide are heated for 16 hours to 80° C. After cooling, the suspension is filtered with suction and the residue is washed twice with acetone and dried at 50° C. for 16 hours in vacuo, affording 37.5 g (82.5% of theory) of 2-(N'-methyl-4'-pyridylium)-s-triazine-bromide with a melting point of 278°–280° C.

| Analysis: | $C_9H_9BrN_4$ (M = 253.11) | | | |
|---|---|---|---|---|
| | C | H | Br | N |
| calculated: | 42.70 | 3.59 | 31.57 | 22.14 % |
| found | 42.63 | 3.58 | 31.53 | 22.01 % |

EXAMPLE 3

2-(N'-Methyl-4'-pyridylium)-s-triazine-tribromide 1.83 g of sodium bromide (0.0178 mole) are dissolved in 200 ml of water and 2.32 g (0.72 ml) of bromine (0.0145 mole) are added to the solution. To this solution is added a solution of 3.6 g (0.0142 mole) of 2-(N'-methyl-4'-pyridylium)-s-triazine-monobromide of Example 2 in 25 ml of water. The mixture is stirred for 10 minutes at 25°–30° C. The suspension is filtered with suction, the residue washed twice with a small amount of water and dried at 50° C. in vacuo, giving 3.3 g (56% of theory) of 2-(N'-methyl-4'-pyridylium)-s-triazine-tribromide with a melting point of 137°–138° C.

| Analysis: | $C_9H_9Br_3N_4$ (M = 412.942) | | | |
|---|---|---|---|---|
| | C | H | N | Br |
| calculated: | 26.23 | 2.20 | 13.60 | 58.17 % |
| found: | 26.52 | 2.23 | 13.71 | 57.90% |

EXAMPLE 4

15.8 g (0.1 mole) of 2-(4'-pyridyl)-s-triazine are dissolved in 250 ml of chloroform and 15 ml of allyl bromide and the solution is boiled for 20 hours at 100° C. bath temperature. After filtration (hot), the mother liquor is concentrated and the residue is treated with acetone. The precipitate is collected with suction, washed with acetone and dried in vacuo, affording 25.8 g (92% of theory) of 2-(N'-allyl-4'-pyridylium)-s-triazine-bromide with a melting point of 170°–172° C.

| Analysis: | $C_{11}H_{11}N_4 \cdot Br$ (M = 279.146) | | | | |
|---|---|---|---|---|---|
| | C | H | N | Br | $H_2O$ |
| calculated: | 47.32 | 3.97 | 20.07 | 28.63 | |
| found: | 46.76 | 4.06 | 19.82 | 28.48 | 0.7 |

EXAMPLE 5

(a) 15.7 g of iso-nicotinic acid amidine hydrochloride (0.1 mole) are suspended in 26.1 g of acetiminoethyl ether (0.3 mole). The suspension is heated to 55° C. and the reaction is exothermic. After stirring for 15 minutes at 50°–60° C., the temperature falls and a precipitate forms. The precipitate is collected with suction and washed with acetonitrile. The mother liquor is extracted with ether after dilution with water. The ethereal extract is dried over magnesium sulphate and concentrated. The residue is recrystallised from hexane to give 11.5 g (62% of theory) of 2-(4'-pyridyl)-4,6-dimethyl-s-triazine with a melting point of 72°–74° C. The melting point of the pure product is 76°–77° C.

(b) 1.7 g of the above triazine (0.00914 mole) are dissolved in 30 ml of methylene chloride and 3 ml of methyl iodide are added. After boiling at 60° C. bath temperature for 16 hours, the mixture is filtered and concentrated, giving 3.1 g (97% of theory) of 2-(N'-methyl-4'-pyridylium)-4,6-dimethyl-s-triazine-iodide with a melting point of 171°–173° C.

| Analysis: | $C_{11}H_{13}N_4 \cdot I$ (M = 328.156) | | | |
|---|---|---|---|---|
| | C | H | N | I |
| calculated: | 40.26 | 3.99 | 17.07 | 38.67% |
| found: | 39.34 | 3.91 | 15.73 | 37.43% |

EXAMPLE 6

(a) 15 g (1 mole) of 4-carbethoxypyridine, 8.7 g of acetiminoethyl ether (1 mole) and 8.1 g (1 mole) of formamidine hydrochloride is stirred for 5 hours at 50°–55° C. and then diluted with water. The suspension is filtered with suction and the residue is washed with water (2-(4'-pyridyl)-s-triazine, m.p. pure 186° C.). The filtrate is extracted with ether and the ethereal extract is dried over magnesium sulphate and concentrated. The resultant mixture is purified by fractional recrystallisation from hexane, giving 3 g of 2-methyl-4-(pyrid-4-yl)-s-triazine with a melting point of 99°–102° C.

(b) A mixture of 0.4 g of 2-methyl-4-(pyrid-4'-yl)-s-triazine (0.00232 mole), 5 ml of methyl iodide and 10 ml of absolute chloroform is boiled for 16 hours at 80° C., then cooled and filtered with suction. The residue of the concentrated mother liquor is suspended in acetone and filtered with suction, affording 0.5 g (62% of theory) of 2-methyl-4-(N-methylpyridylium-4')-s-triazine-iodide with a melting point of 193°–195° C.

The following table lists the quaternary salts of the formula I obtained according to the foregoing Examples and also those prepared in analogous manner:

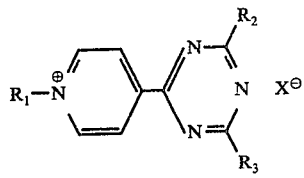

The novel quaternary salts of the formula I are particularly suitable for the defoliation and desiccation of unlignified parts of plants above the ground and also for use as contact herbicides (for example against Cyperus). The active compounds are particularly suitable for the defoliation and desiccation of cotton plants, leguminous plants, sorghum, soya, potatoes and vines before harvesting, without detriment to the after-ripening. Moreover, plants which are destined for despatch, such as ornamentals (chrysenthemums, roses), or tree nursery material (ornamental shrubs and trees), as well as plant material intended for obtaining seeds, can also be treated with these active compounds. Some of the active compounds also possess bacteriostatic and fungistatic action and can also be used as growth inhibitors.

The novel active compounds of the formula I have a broader activity spectrum and are more effective than the post-emergent herbicides of U.S. Pat. Nos. 3,737,299; 3,804,612 and 3,682,617. For example, the novel active compounds of the formula I are superior in their action as contact herbicides and defoliants to the "Cyperquat" (4-phenyl-1-methyl-pyridinium chloride) of the formula

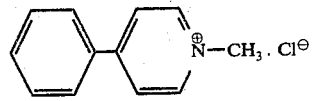

described in U.S. Pat. No. 3,737,299.

The technical usefulness of the quaternary salts of the present invention for defoliation, desiccation, and as

| Compound | $R_1$ | $R_2$ | $R_3$ | $X^\ominus$ | Melting point in ° C |
|---|---|---|---|---|---|
| 1 | $CH_3$ | H | H | $I^-$ | 272° |
| 2 | $CH_3$ | H | H | $Br_3^-$ | 139° |
| 3 | $CH_3$ | H | H | $Cl^-$ | 216° |
| 4 | $CH_3$ | H | H | $Br^-$ | 278° |
| 5 | $CH_3$ | H | H | $CH_3OSO_2O^-$ | oil |
| 6 | $C_2H_5$ | H | H | $Br^-$ | 188–191° |
| 7 | $C_2H_5$ | H | H | $I^-$ | 202° |
| 8 | $n\text{-}C_3H_7$ | H | H | $Br^-$ | 180° |
| 9 | $i\text{-}C_3H_7$ | H | H | $I^-$ | 224° |
| 10 | $n\text{-}C_4H_9$ | H | H | $Br^-$ | oil |
| 11 | $n\text{-}C_4H_9$ | H | H | $I^-$ | 122° |
| 12 | $n\text{-}C_5H_{11}$ | H | H | $I^-$ | viscous oil |
| 13 | $n\text{-}C_8H_{17}$ | H | H | $Br^-$ | 145° |
| 14 | $C_{12}H_{25}$ | H | H | $Br^-$ | >105° |
| 15 | Allyl | H | H | $Br^-$ | 170° |
| 16 | $C_2H_5\text{-}O\text{-}C_2H_4-$ | H | H | $Br^-$ | solid |
| 17 | $C_2H_5\text{-}O\text{-}CO\text{-}CH_2-$ | H | H | $Br^-$ | 195° |
| 18 | benzyl | H | H | $Br^-$ | 129° |
| 19 | $CH_3$ | $CH_3$ | $CH_3$ | $I^-$ | 171° |
| 20 | $CH_3$ | $CH_3$ | $CH_3$ | $Br^-$ | |
| 21 | $C_2H_5$ | $CH_3$ | $CH_3$ | $I^-$ | 217° |
| 22 | $CH_3$ | H | $CH_3$ | $I^-$ | 195° |
| 23 | $CH_3$ | $CH_3$ | $i\text{-}C_3H_7$ | $I^-$ | |
| 24 | $CH_3$ | $n\text{-}C_4H_9$ | $n\text{-}C_4H_9$ | $I^-$ | |
| 25 | $CH_3$ | $CCl_3$ | $CCl_3$ | $I^-$ | |
| 26 | $CH_3$ | $CF_3$ | $CF_3$ | $I^-$ | |
| 27 | $CH_3OOC\text{-}CH-$ | H | H | $Br^-$ | |
| 28 | $CH_3\text{-}CO\text{-}CH_2-$ | H | H | $Cl^-$ | |
| 29 | $NC\text{-}CH_2-$ | H | H | $Cl^-$ | |
| 30 | $NH_2\text{-}CO\text{-}CH_2-$ | H | H | $I^-$ | |
| 31 | $^\ominus OOC\text{-}CH_2-$ | H | H | | |
| 32 | $(CH_3)_2\text{-}N\text{-}CO\text{-}CH_2$ | H | H | $Br^-$ | |
| 33 | $n\text{-}C_4H_9\text{-}OOC\text{-}CH_2$ | H | H | $Br^-$ | |
| 34 | $CH_2=CH\text{-}CH-$<br>$\|$<br>$CH_3$ | H | H | $Br^-$ | |
| 35 | $CH_2=C\text{-}CH_2-$<br>$\|$<br>$Cl$ | H | H | $Cl^-$ | |
| 36 | $CH_3OOC\text{-}CH_2-$ | H | H | $Br^-$ | | contact herbicides, is illustrated by the following experimental trials.

1. Defoliation, desiccation

The active compounds are applied as a 0.5% aqueous suspension (obtained from a 25% emulsifiable concentrate) to cotton plants approx. 20 cm in height shortly before the emergence of the 3rd leaf. Only the leaf surface and stem of each plant are treated. The rate of application corresponded to 4 kg of active substance per hectare. The plants are then kept in a greenhouse at 24° to 26° C. and 45 to 60% relative humidity. The test is evaluated after 14 days in accordance with the following rating:

| | | |
|---|---|---|
| 9 = 0 to 11 % defoliation or desiccation | ⎫ | referred to |
| 8 = 12 to 22 % defoliation or desiccation | ⎬ | the total |
| 1 = 89 to 100 % defoliation or desiccation | ⎭ | leaf surface |

The following results were obtained:

| Compound No. of table | Defoliation | Desiccation |
|---|---|---|
| "Cyperquat" (U.S. Pat. No. 3,737,299) | 9 | 8 |
| 3 | 1 | 1 |
| 6 | 1 | 1 |
| 10 | 1 | 1 |

2. Selective contact herbicidal action

The following cultivated plants and species of weed are reared in plastic pots:

| cultivated plants | species of weed |
|---|---|
| Avena sativa (oats) | Setaria italica |
| Triticum vulgare (wheat) | Solanum |
| Oryza (upland rice) | Sinapis alba |
| Hordeum (barley) | Stellaria media |
| Zea (maize) | Digitaria sanguinalis |
| | Echinochloa crus galli |
| | Sida spinosa |
| | Sesbania exaltata |
| | Amaranthus retr. |
| | Galium aparine |
| | Pastinaca sativa |
| | Matricaria chamomilla |

After approx. 2 weeks, the plants are treated with aqueous suspensions of the active compounds, prepared from the described wettable powders or emulsifiable concentrates. Thereafter the plants are kept at 22° to 25° C. and 50 to 70% relative humidity. The test is evaluated after 15 days. At rates of application of 2 kg of active compound per hectare, the tested quaternary salts of the table showed an excellent contact herbicidal action on the weeds, whilst the cultivated plants showed virtually no signs of injury:

The compositions of the invention are prepared in known manner by homogeneously mixing and/or grinding active compounds of the formula I with suitable carriers, with or without the addition of dispersants or solvents which are inert to the active compounds. The active compounds may be used in the following formulations:

Solid formulations:

dusts, tracking agents, granules (coated granules, impregnated granules and homogeneous granules);

active substance concentrates which are dispersible in water:

wettable powders, pastes, emulsions; emulsifiable concentrates;

Liquid formulations:

solutions, particularly in water.

Storable solid formulations (dusts, tracking agents, granules), are prepared by mixing the active compounds with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

The particle size of the carriers for dusts is advantageously up to about 0.1 mm, for tracking agents from about 0.075 to 0.2 mm, and for granules 0.2 mm or larger.

The solid formulations contain the active substances in concentrations from 0.5% to 80%.

To these mixtures can also be added additives which stabilize the active substance and/or non-ionic, anionic and cationic surface active substances, which for example improve the adhesion of the active ingredients on plants or parts of plants (tackifiers and adhesives) and/or ensure a better wettability (wetting agents) and dispersibility (dispersing agents). Examples of suitable adhesives are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, ligninsulphonic acids, the alkali metal and alkaline earth metal salts thereof, polyethylene glycol ether (carbowax), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersbile concentrates of the active compounds, i.e. wettable powders, pastes and emulsifiable concentrates, are compositions which can be diluted with water to any desired concentration. They consist of active compound, carrier, optionally additives which stabilize the active compound, surface-active substances and anti-foam agents, and, optionally, solvents. The concentration of active compound in these compositions is from 5-80%.

Wettable powders and pastes are obtained by mixing and grinding the active compounds with dispersing agents and pulverulent carriers in suitable devices until homogeneity is attained.

Suitable carriers are, for example, those mentioned for the solid formulations. It is often advantageous to use mixtures of different carriers.

As dispersing agents there can be used, for example, condensation products of sulphonated naphthalene and sulphonated naphthalene derivatives with formaldehyde, condensation products of naphthalene or naphthalenesulphonic acids with phenol and formaldehyde, as well as alkali, ammonium and alkaline earth metal salts of ligninsulphonic acid; in addition, alkylaryl sulphonates, alkali and alkaline earth metal salts of dibutylnaphthalenesulphonic acid, fatty alcohol sulphates, such as salts of sulphated hexadecanols, heptadecanols, octadecanols, and salts of sulphated fatty alcohol glycol ethers, the sodium salt of oleylmethyl tauride, ditertiary acetylene glycols, dialkyl dilauryl ammonium chloride and fatty acid alkali salts and alkaline earth metal salts.

Suitable anti-foam agents are silicones.

The active compounds are so mixed, ground sieved and strained with the additives mentioned above that, in wettable powders, the solid particle size of 0.02 to 0.04 mm and in pasts, of 0.03 mm is not exceeded. Emulsifiable concentrates and pastes are manufactured by using dispersing agents, such as those cited in the previous paragraphs, organic solvents and water. Examples of suitable solvents are: alcohols, benzene, xylenes, toluene, dimethyl sulphoxide, and mineral oil fractions which boil between 120° and 350° C. The solvents must be practically odourless, not phytotoxic, inert to the active compounds and may not be readily inflammable.

When preparing non-aqueous stable preparations, care should be taken to formulate them as anhydrous preparations or to add dehydrating agents in order to to increase their storage life and keeping quality.

Furthermore, the compositions of the invention can be applied in the form of solutions. For this purpose the active compounds or several active compounds of the general formula I are dissolved in suitable organic solvents, mixtures of solvents, in water, or in mixtures of organic solvents with water. Alcohols, dialkylsulphoxides, such as dimethyl sulphoxide, N,N-dialkylated amides, such as dimethyl formamide, singly or in admixture with one another or with water, can be used as organic solvents. The solutions contain the active compounds in a concentration range from 1% to 20%. These solutions can be applied either with a propellant gas (as spray) or with special sprays (as aerosol).

The compositions of the invention can be mixed with other biocidally active substances or agents. Thus in order to broaden the activity spectrum the compositions may contain, for example, insecticides, fungicides, bactericides, fungistats, bacteriostats or nematocides, in addition to the compounds of the formula I. The compositions of the invention can also contain plant fertilisers, trace elements etc. In addition, they can also contain additives which stabilise the active compounds.

Formulations of the novel active compounds of the formula I are described hereinafter. Parts denote parts by weight.

Powder Concentrate

The following substances are homogeneously mixed with one another and ground to prepare a 10% powder concentrate:

10 parts of 2-(N'-methyl-4'-pyridylium)-s-triazineiodide,
0.6 parts of sodium dibutylnaphthylsulphonate,
1 part of naphthalenesulphonic acid/phenolsulphonic acid/formaldehyde concentrate (3:2:1),
10 parts of sodium aluminium silicate,
78.4 parts of kaolin.

Wettable Powder

The following constituents are used for prepare (a) a 50%, (b) a 25% and (c) a 10% wettable powder:

(a)

50 parts of 2-(N'-methyl-4'-pyridylium)-s-triazineiodide,
5 parts of sodium dibutylnaphthylsulphonate,
3 parts of naphthalenesulphonic acid/phenolsulphonic acid/formaldehyde condensate (3:2:1),
20 parts of kaolin,
22 parts of Champagne chalk;

(b)

25 parts of 2-(N'-ethyl-4'-pyridylium)-s-triazinebromide,
5 parts of sodium oleylmethyltauride,
2.5 parts of naphthalenesulphonic acid/formaldehyde condensate,
0.5 part of carboxymethyl cellulose,
5 parts of neutral potassium aluminium silicate,
62 parts of kaolin;

(c)

10 parts of 2-(N'-methyl-4'-pyridylium)-4,6-dimethyl-s-triazine-bromide,
3 parts of a mixture of the sodium salts of saturated fatty alcohol sulphates,
5 parts of naphthalenesulphonic acid/formaldehyde condensate.
82 parts of kaolin.

The respective active substance is applied to the corresponding carriers (kaolin and chalk) and then these are mixed and ground, to yield wettable powders of excellent wettability and suspension powder. By diluting these wettable powders with water it is possible to obtain suspensions of the desired concentration of active substance.

Paste

The following substances are used to manufacture a 45% paste:

45 parts of 2-(N'-ethyl-4'-pyridylium)-4-methyl-6-propyl-s-triazine-iodide,
5 parts of sodium aluminium silicate,
14 parts of cetyl polyglycol ether with 8 moles of the ethylene oxide,
1 part of oleyl polyglycol ether with 5 moles of the ethylene oxide,
2 parts of spindle oil,
10 parts of polyethylene glycol,
23 parts of water.

The active substance is homogeneously mixed with the additives in appropriate devices and ground. A paste is obtained from which, by dilution with water, it is possible to manufacture suspensions of the desired concentration of active substance.

Emulsifiable Concentrate

The following ingredients are mixed to manufacture a 25% emulsifiable concentrate:

25 parts of 2-(N'-methyl-4'-pyridylium)-s-triazineiodide (or chloride),
5 parts of a mixture of nonylphenolpolyoxy-ethoxyethylene and calcium dodecylenesulphonate,
35 parts of 3,5,5-trimethyl-2-cyclohexan-1-one,
35 parts of dimethyl formamide.

This concentrate can be diluted with water to give emulsions in the desired concentrations.

What is claimed is:
1. A compound of the formula

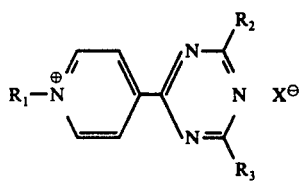

in which $R_1$ represents an alkyl group of from 1 to 12 carbon atoms or a $C_1$–$C_4$ alkyl group substituted by halogen, $C_1$–$C_4$ alkoxy, cyano, phenyl, carboxyl, $C_1$–$C_4$ alkoxycarbonyl, $C_1$–$C_4$ alkylcarbonyl, aminocarbonyl, mono- and di-($C_1$–$C_4$) alkylaminocarbonyl, or $R_1$ represents $C_3$–$C_7$ alkenyl or $C_3$–$C_7$ haloalkenyl, each of $R_2$ and $R_3$ independently represents hydrogen, alkyl from 1 to 4 carbon atoms, haloalkyl from 1 to 4 carbon atoms; and $X^\ominus$ is a halogen anion, $Br_e^\ominus$ or $CH_3OSO_2O^\ominus$.

2. A compound according to claim 1 which is of the formula

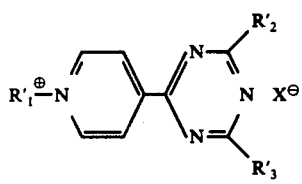

wherein $R'_1$ is alkyl of from one to five carbon atoms, each of $R'_2$ and $R'_3$ represents hydrogen and $X^\ominus$ is chloride, bromide, iodide or methosulphate.

3. The compound of claim 2 which is 2-(N'-methyl-4'-pyridylium)-s-triazine chloride.

4. The compound of claim 2 which is 2-(N'-ethyl-4'-pyridylium)-s-triazine bromide.

5. The compound of claim 2 which is 2-(N'-n-butyl-4'-pyridylium)-s-triazine bromide.

6. A composition for improving the yield and facilitating the harvesting of crops which comprises (1) as active ingredient an effective amount of a compound of the formula.

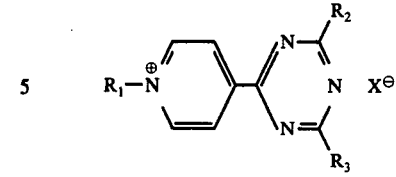

in which $R_1$ represents an alkyl group of from 1 to 12 carbon atoms or a $C_1$–$C_4$ alkyl group substituted by halogen, $C_1$–$C_4$ alkoxy, cyano, phenyl, carboxyl, $C_1$–$C_4$ alkoxycarbonyl, $C_1$–$C_4$ alkycarbonyl, aminocarbonyl, mono- and di-($C_1$–$C_4$)alkylaminocarbonyl, or $R_1$ represents $C_3$–$C_7$ alkenyl or $C_3$–$C_7$ haloalkenyl, each of $R_2$ and $R_3$ independently represents hydrogen, alkyl from 1 to 4 carbon atoms, haloalkyl from 1 to 4 carbom atoms; and $X^\ominus$ is a halogen anion, $Br_3^\ominus$ or $CH_3OSO_2O^\ominus$ and (2) a suitable carrier therefor.

7. A composition according to claim 6 in which the active ingredient is a compound wherein $R_1$ is alkyl from one to five carbon atoms, $R_2$ and $R_3$ both represent hydrogen and $X^\ominus$ is chloride, bromide, iodide or methosulphate.

8. A method for improving the yield and facilitating the harvesting of crops which comprises applying to a crop culture in an amount sufficient to influence plant growth, a composition according to claim 6.

9. A method according to claim 8 which comprises applying the said composition in an amount sufficient to control weeds in the crop.

10. A method according to claim 8 where the composition is applied to cotton and potatoe plants in a an amount sufficient to attain defoliation and desiccation.

11. A method according to claim 10 in which the compound 2-(N'-methyl-4'-pyridylium)-s-triazine chloride is the active ingredient of the composition used for the defoliation and desiccation.

12. A method according to claim 10 in which the compound 2-(N'-ethyl-4'-pyridylium)-s-triazine bromide is the active ingredient of the composition used for defoliation and desiccation.

13. A method according to claim 10 in which the compound 2-(N'-n-butyl-4'-pyridylium)-s-triazine bromide is the active ingredient of the composition used for defoliation and desiccation.

* * * * *